(12) United States Patent
Bourrie et al.

(10) Patent No.: US 6,344,464 B1
(45) Date of Patent: Feb. 5, 2002

(54) USE OF TETRAHYDROPYRIDINE DERIVATIVES TO PREPARE MEDICINES FOR TREATING DISEASES CAUSING DEMYELINATION

(75) Inventors: Bernard Bourrie, Saint Gély du Fesc; Pierre Casellas, Montpellier; Jean-Pierre Maffrand, Portet, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/403,507

(22) PCT Filed: Apr. 17, 1998

(86) PCT No.: PCT/FR98/00774

§ 371 Date: Apr. 18, 2000

§ 102(e) Date: Apr. 18, 2000

(87) PCT Pub. No.: WO98/48802

PCT Pub. Date: Nov. 5, 1998

(30) Foreign Application Priority Data

Apr. 29, 1997 (FR) ............................................. 97 05275

(51) Int. Cl.⁷ ............................................. A61K 31/445
(52) U.S. Cl. ...................................... 514/315; 514/318
(58) Field of Search .................................. 514/315, 318

(56) References Cited

U.S. PATENT DOCUMENTS

| 4,521,428 A | 6/1985 | Nisato et al. ............... 514/277 |
| 5,229,389 A | 7/1993 | Coude et al. ................ 514/260 |

FOREIGN PATENT DOCUMENTS

| EP | 101381 | 12/1985 |
| EP | 458696 | 1/1996 |
| FR | 2740343 | 4/1997 |
| WO | WO93/11107 | 6/1993 |
| WO | WO97/01536 | 1/1997 |

OTHER PUBLICATIONS

Fournier et al., Neuroscience, vol. 55, No. 3, pp. 629–641, 1993.
Ruigt et al., Neuroscience Letters, vol. 203, No. 1, pp. 9–12, 1996.

*Primary Examiner*—Theodore J. Criares
(74) *Attorney, Agent, or Firm*—Paul E. Dupont; Michael D. Alexander

(57) ABSTRACT

The invention relates to the use of tetrahydropyridine derivatives of the formula

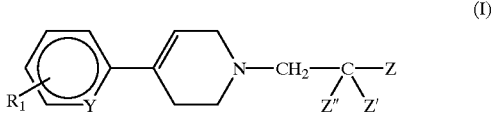

(I)

in which:
R$_1$ is a halogen or a CF$_3$, (C$_1$–C$_4$)alkyl or (C$_1$–C$_4$)alkoxy group;
Y is a nitrogen atom or a CH group;
Z' and Z" are each hydrogen or a (C$_1$–C$_3$)alkyl group, or one is hydrogen and the other is a hydroxyl group, or the two together are an oxo group; and
Z is:
  a phenyl radical;
  a phenyl radical monosubstituted by a substituent X, X being:
   (a) a (C$_1$–C$_6$)alkyl, (C$_1$–C$_6$)alkoxy, (C$_3$–C$_7$) carboxyalkyl, (C$_1$–C$_4$)alkoxycarbonyl(C$_1$–C$_6$) alkyl, (C$_3$–C$_7$)carboxyalkoxy or (C$_1$–C$_4$) alkoxycarbonyl(C$_1$–C$_6$)alkoxy group;
   (b) a group selected from (C$_3$–C$_7$)cycloalkyl, (C$_3$–C$_7$)cycloalkoxy, (C$_3$–C$_7$)cycloalkylmethyl, (C$_3$–C$_7$)cycloalkylamino and cyclohexenyl, it being possible for said group to be substituted by a halogen, hydroxy, (C$_1$–C$_4$)alkoxy, carboxy, (C$_1$–C$_4$)alkoxycarbonyl, amino or mono- or di- (C$_1$–C$_4$)alkylamino group; or
   (c) a group selected from phenyl, phenoxy, phenylamino, N—(C$_1$–C$_3$)alkyl-phenylamino, phenylmethyl, phenylethyl, phenylcarbonyl, phenylthio, phenylsulfonyl, phenylsulfinyl and styryl, it being possible for said group to be monosubstituted or polysubstituted on the phenyl group by a halogen, CF$_3$, (C$_1$–C$_4$)alkyl, (C$_1$–C$_4$) alkoxy, cyano, amino, mono- or di-(C$_1$–C$_4$) alkylamino, (C$_1$–C$_4$)acylamino, carboxy, (C$_1$–C$_4$) alkoxycarbonyl, aminocarbonyl, mono- or di- (C$_1$–C$_4$)alkylaminocarbonyl, amino(C$_1$–C$_4$)alkyl, hydroxy(C$_1$–C$_4$)alkyl or halogeno(C$_1$–C$_4$)alkyl group;
  a phenyl radical disubstituted by a substituent R$_2$, R$_2$ being a halogen or a hydroxy, methyl, ethyl, (C$_3$–C$_6$) alkyl, (C$_1$–C$_4$)alkoxy or trifluoromethyl group, and by a substituent X, X being as defined above;
  a 1-naphthyl or 2-naphthyl radical; or
  a 1-naphthyl or 2-naphthyl radical substituted in the 5-, 6-, 7- and/or 8-positions by one or two hydroxy groups, one or two (C$_1$–C$_4$)alkoxy groups or a 6,7-methylenedioxy group;
or Z" is hydrogen and Z and Z' are each independently an unsubstituted or mono-, di- or tri-substituted phenyl group,
or a pharmaceutically acceptable salt and solvate thereof, for the preparation of pharmaceutical compositions intended for treating diseases which cause demyelination.

29 Claims, No Drawings

USE OF TETRAHYDROPYRIDINE DERIVATIVES TO PREPARE MEDICINES FOR TREATING DISEASES CAUSING DEMYELINATION

The present invention relates to the use of certain tetrahydropyridines for the preparation of drugs intended for the treatment of diseases which cause destruction of myelin.

These pathological conditions share the characteristic of being of inflammatory or autoimmune origin and of causing loss of myelin in the central nervous system. It is possible to draw a distinction principally between chronic pathological conditions, such as multiple sclerosis, and acute pathological conditions, such as acute disseminated encephalomyelitis and acute hemorrhagic leukoencephalitis. Among these pathological conditions, multiple sclerosis is the most widespread and leads to very serious sensory and visual motor dysfunctions.

No effective therapy is currently available for these diseases, and the treatments are limited to symptomatic treatments aimed at improving spastic hypertonia, fatigue and pain, or, since the origin of these pathological conditions is often said to be autoimmune, symptomatic treatments aimed at suppressing the immunological response.

WO 93/11107 describes a class of N-hydroxyalkyl-1,2,3,6-tetrahydropyridines as protectors against the damage caused by hypoxia.

EP 0 101 381 describes trifluoromethylphenyltetrahydropyridine derivatives having an anorexigenic activity and EP 0 458 696 describes their neuroprotective effects.

WO 97/01536 describes 1-phenylalkyl-1,2,3,6-tetrahydropyridines also having a neurotrophic and neuroprotective activity.

It has now been found that certain tetrahydropyridines exert a beneficial action on diseases which cause destruction of myelin.

Thus the present invention relates to the use of a compound of formula (I):

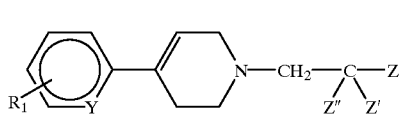

(I)

in which:
  $R_1$ is a halogen or a $CF_3$, $(C_1-C_4)$alkyl or $(C_1-C_4)$alkoxy group;
  Y is a nitrogen atom or a CH group;
  Z' and Z" are each hydrogen or a $(C_1-C_3)$alkyl group, or one is hydrogen and the other is a hydroxyl group, or the two together are an oxo group; and
  Z is:
    a phenyl radical;
    a phenyl radical monosubstituted by a substituent X, X being:
      (a) a $(C_1-C_6)$alkyl, $(C_1-C_6)$alkoxy, $(C_3-C_7)$carboxyalkyl, $(C_1-C_4)$alkoxycarbonyl$(C_1-C_6)$alkyl, $(C_3-C_7)$carboxyalkoxy or $(C_1-C_4)$alkoxycarbonyl$(C_1-C_6)$alkoxy group;
      (b) a group selected from $(C_3-C_7)$cycloalkyl, $(C_3-C_7)$cycloalkoxy, $(C_3-C_7)$cycloalkylmethyl, $(C_3-C_7)$cycloalkylamino and cyclohexenyl, it being possible for said group to be substituted by a halogen, hydroxyl, $(C_1-C_4)$alkoxy, carboxyl, $(C_1-C_4)$alkoxycarbonyl, amino or mono- or di-$(C_1-C_4)$alkylamino; or
      (c) a group selected from phenyl, phenoxy, phenylamino, N—$(C_1-C_3)$alkylphenylamino, phenylmethyl, phenylethyl, phenylcarbonyl, phenylthio, phenylsulfonyl, phenylsulfinyl and styryl, it being possible for said group to be monosubstituted or polysubstituted on the phenyl group by a halogen, $CF_3$, $(C_1-C_4)$alkyl, $(C_1-C_4)$alkoxy, cyano, amino, mono- or di-$(C_1-C_4)$alkylamino, $(C_1-C_4)$acylamino, carboxyl, $(C_1-C_4)$alkoxycarbonyl, aminocarbonyl, mono- or di-$(C_1-C_4)$alkylaminocarbonyl, amino$(C_1-C_4)$alkyl, hydroxy$(C_1-C_4)$alkyl or halogeno$(C_1-C_4)$alkyl;
    a phenyl radical disubstituted by a substituent $R_2$, $R_2$ being a halogen or a hydroxyl, methyl, ethyl, $(C_3-C_6)$alkyl, $(C_1-C_4)$alkoxy or trifluoromethyl group, and by a substituent X, X being as defined above;
    a 1-naphthyl or 2-naphthyl radical; or
    a 1-naphthyl or 2-naphthyl radical substituted in the 5-, 6-, 7- and/or 8-positions by one or two hydroxyl groups, one or two $(C_1-C_4)$alkoxy groups or a 6,7-methylenedioxy group;
  or Z" is hydrogen and Z and Z' are each independently an unsubstituted or mono-, di- or tri-substituted phenyl group, or one of its pharmaceutically acceptable salts and solvates, for the preparation of pharmaceutical compositions intended for combating diseases which cause demyelination.

According to one advantageous aspect, the invention relates to the use of the compound of formula (I) in which Y is CH, $R_1$ is trifluoromethyl and Z' and Z" are hydrogen, or one of its pharmaceutically acceptable salts and solvates.

According to one preferred aspect, the invention relates to the use of the compound of formula (I) in which Y is CH, $R_1$ is trifluoromethyl, Z' and Z" are hydrogen and Z is a 2-naphthyl, 6,7-dimethoxy-2-naphthyl or 6,7-methylenedioxy-2-naphthyl group, or one of its pharmaceutically acceptable salts and solvates.

According to another advantageous aspect, the invention relates to the use of the compound of formula (I) in which Y is CH, $R_1$ is trifluoromethyl, Z' and Z" are hydrogen and Z is either a phenyl radical monosubstituted by a substituent X, X being:
  (a) a $(C_1-C_6)$alkyl, $(C_1-C_6)$alkoxy, $(C_3-C_7)$carboxyalkyl, $(C_1-C_4)$alkoxycarbonyl$(C_1-C_6)$alkyl, $(C_3-C_7)$carboxyalkoxy or $(C_1-C_4)$alkoxycarbonyl$(C_1-C_6)$alkoxy group;
  (b) a group selected from $(C_3-C_7)$cycloalkyl, $(C_3-C_7)$cycloalkoxy, $(C_3-C_7)$cycloalkylmethyl, $(C_3-C_7)$cycloalkylamino and cyclohexenyl, it being possible for said group to be substituted by a halogen, hydroxyl, $(C_1-C_4)$alkoxy, carboxyl, $(C_1-C_4)$alkoxycarbonyl, amino or mono- or di-$(C_1-C_4)$alkylamino; or
  (c) a group selected from phenyl, phenoxy, phenylamino, N—$(C_1-C_3)$alkyl-phenylamino, phenylmethyl, phenylethyl, phenylcarbonyl, phenylthio, phenylsulfonyl, phenylsulfinyl and styryl, it being possible for said group to be monosubstituted or polysubstituted on the phenyl group by a halogen, $CF_3$, $(C_1-C_4)$alkyl, $(C_1-C_4)$alkoxy, cyano, amino, mono- or di-$(C_1-C_4)$alkylamino, $(C_1-C_4)$acylamino, carboxyl, $(C_1-C_4)$alkoxycarbonyl, aminocarbonyl, mono- or di-$(C_1-C_4)$alkylaminocarbonyl, amino$(C_1-C_4)$alkyl, hydroxy$(C_1-C_4)$alkyl or halogeno$(C_1-C_4)$alkyl;
or a phenyl disubstituted by $R_2$ and X as defined above, or one of its pharmaceutically acceptable salts and solvates.

According to another advantageous aspect, the invention relates to the use of the compound of formula (I) in which Y is CH, $R_1$ is trifluoromethyl, Z' and Z" are hydrogen and Z is either a phenyl monosubstituted by a group X', X' being a phenyl which is unsubstituted or monosubstituted to trisubstituted by halogen, $CF_3$, $(C_1-C_4)$alkyl, $(C_1-C_4)$alkoxy, cyano, amino, mono- or di-$(C_1-C_4)$alkylamino, $(C_1-C_4)$acylamino, carboxyl, $(C_1-C_4)$alkoxycarbonyl, aminocarbonyl, mono- or di-$(C_1-C_4)$alkylaminocarbonyl, amino$(C_1-C_4)$alkyl, hydroxy$(C_1-C_4)$alkyl or halogeno $(C_1-C_4)$alkyl; or a phenyl substituted by a substituent $R_2$, $R_2$ being a halogen or a hydroxyl, methyl, ethyl, $(C_3-C_6)$alkyl, $(C_1-C_4)$alkoxy or trifluoromethyl group, and by a substituent X', X' being as defined above, or one of its pharmaceutically acceptable salts and solvates.

According to another advantageous aspect, the invention relates to the use of the compound of formula (I) in which Y is CH, $R_1$ is trifluoromethyl, Z' and Z" are hydrogen and Z is a phenyl group substituted in the 3- and 4-positions by a $(C_1-C_6)$alkyl group, or one of its pharmaceutically acceptable salts and solvates.

According to another advantageous aspect, the invention relates to the use of the compound of formula (I) in which Y is CH, $R_1$ is trifluoromethyl, Z" is hydrogen and Z and Z', which are identical, are each a phenyl group; a phenyl group substituted in the 2-, 3- or 4-position by a fluorine or chlorine atom or by a methyl, ethyl, n-propyl, i-propyl, n-butyl, i-butyl, s-butyl, t-butyl, trifluoromethyl, cyano, methoxy, methylthio, methylsulfonyl, ethoxy, ethylthio, ethylsulfonyl, $(C_1-C_3)$alkoxycarbonyl or di$(C_1-C_3)$alkylaminocarbonyl group; a phenyl group disubstituted in the 2,4-, 3,4-, 3,5- or 2,6-positions by a chlorine or fluorine atom or by a methyl, ethyl, trifluoromethyl, cyano or methoxy group; or a phenyl group trisubstituted in the 3,4,5-, 2,4,5- or 2,4,6-positions by a chlorine or fluorine atom or by a methyl, ethyl, trifluoromethyl, cyano or methoxy group, or one of its pharmaceutically acceptable salts and solvates.

Particularly advantageous compounds according to the present invention are the following compounds:

1-(2-naphth-2-ylethyl)-4-(3-trifluoromethylphenyl)-1,2,3,6-tetrahydropyridine;

1-[2-(6,7-dimethoxynaphth-2-yl)ethyl]-4-(3-trifluoromethylphenyl)-1,2,3,6-tetrahydropyridine;

1-[2-(6,7-methylenedioxynaphth-2-yl)ethyl]-4-(3-trifluoromethylphenyl)-1,2,3,6-tetrahydropyridine;

1-[2-(4-isobutylphenyl)propyl]-4-(3-trifluoromethylphenyl)-1,2,3,6-tetrahydropyridine;

1-[(2S)-2-(4-isobutylphenyl)propyl]-4-(3-trifluoromethylphenyl)-1,2,3,6-tetrahydropyridine;

1-[(2R)-2-(4-isobutylphenyl)propyl]-4-(3-trifluoromethylphenyl)-1,2,3,6-tetrahydropyridine;

1-[2-(4-isobutylphenyl)ethyl]-4-(3-trifluoromethylphenyl)-1,2,3,6-tetrahydropyridine;

1-[2-(4-tert-butylphenyl)ethyl]-4-(3-trifluoromethylphenyl)-1,2,3,6-tetrahydropyridine;

1-[2-(4-isobutylphenyl)-2-methylpropyl]-4-(3-trifluoromethylphenyl)-1,2,3,6-tetrahydropyridine;

1-[2-(4-isopropylphenyl)ethyl]-4-(3-trifluoromethylphenyl)-1,2,3,6-tetrahydropyridine;

1-[2-(3'-chlorobiphenyl-4-yl)ethyl]-4-(3-trifluoromethylphenyl)-1,2,3,6-tetrahydropyridine;

1-[2-(2'-chlorobiphenyl-4-yl)ethyl]-4-(3-trifluoromethylphenyl)-1,2,3,6-tetrahydropyridine;

1-[2-(4'-chlorobiphenyl-4-yl)ethyl]-4-(3-trifluoromethylphenyl)-1,2,3,6-tetrahydropyridine;

1-[2-(4'-fluorobiphenyl-4-yl)ethyl]-4-(3-trifluoromethylphenyl)-1,2,3,6-tetrahydropyridine;

1-[2-(3'-trifluoromethylbiphenyl-4-yl)ethyl]-4-(3-trifluoromethylphenyl)-1,2,3,6-tetrahydropyridine;

1-[2-(4-cyclohexylphenyl)ethyl]-4-(3-trifluoromethylphenyl)-1,2,3,6-tetrahydropyridine;

1-[2-(biphenyl-4-yl)ethyl]-4-(4-fluorophenyl)-1,2,3,6-tetrahydropyridine;

1-[2-(biphenyl-4-yl)-2-methylpropyl]-4-(3-trifluoromethylphenyl)-1,2,3,6-tetrahydropyridine;

1-[2-(4-phenoxyphenyl)ethyl]-4-(3-trifluoromethylphenyl)-1,2,3,6-tetrahydropyridine;

1-[2-(4-benzylphenyl)ethyl]-4-(3-trifluoromethylphenyl)-1,2,3,6-tetrahydropyridine;

1-[2-(4-n-butylphenyl)ethyl]-4-(3-trifluoromethylphenyl)-1,2,3,6-tetrahydropyridine;

1-[2-(biphenyl-4-yl)ethyl]-4-(3-trifluoromethylphenyl)-1,2,3,6-tetrahydropyridine;

1-[2-(4-n-butoxyphenyl)ethyl]-4-(3-trifluoromethylphenyl)-1,2,3,6-tetrahydropyridine;

1-[2-(3,4-diethylphenyl)ethyl]-4-(3-trifluoromethylphenyl)-1,2,3,6-tetrahydropyridine;

1-[2-(3-methyl-4-pentylphenyl)ethyl]-4-(3-trifluoromethylphenyl)-1,2,3,6-tetrahydropyridine;

1-[2-(4-methyl-3-pentylphenyl)ethyl]-4-(3-trifluoromethylphenyl)-1,2,3,6-tetrahydropyridine;

1-[2-(3,4-diethylphenyl)ethyl]-4-(6-chloropyrid-2-yl)-1,2,3,6-tetrahydropyridine;

1-(2,2-diphenylethyl)-4-(3-trifluoromethylphenyl)-1,2,3,6-tetrahydropyridine;

1-[2,2-(4,4'-dichlorodiphenyl)ethyl]-4-(3-trifluoromethylphenyl)-1,2,3,6-tetrahydropyridine;

1-[2,2-(3,3'-bistrifluoromethyldiphenyl)ethyl]-4-(3-trifluoromethylphenyl)-1,2,3,6-tetrahydropyridine;

1-[2,2-(4,4'-dimethoxydiphenyl)ethyl]-4-(3-trifluoromethylphenyl)-1,2,3,6-tetrahydropyridine;

1-[2-(4-fluorophenyl)-2-phenylethyl]-4-(3-trifluoromethylphenyl)-1,2,3,6-tetrahydropyridine;

1-(3,3-diphenylpropyl)-4-(3-trifluoromethylphenyl)-1,2,3,6-tetrahydropyridine;

1-[2,2-(4,4'-dichlorodiphenyl)ethyl]-4-(6-chloropyrid-2-yl)-1,2,3,6-tetrahydropyridine;

1-[2-(3'-chlorobiphenyl-4-yl)-2-oxoethyl]-4-(3-trifluoromethylphenyl)-1,2,3,6-tetrahydropyridine;

1-[2-(2'-chlorobiphenyl-4-yl)-2-oxoethyl]-4-(3-trifluoromethylphenyl)-1,2,3,6-tetrahydropyridine;

1-[2-(4'-chlorobiphenyl-4-yl)-2-oxoethyl]-4-(3-trifluoromethylphenyl)-1,2,3,6-tetrahydropyridine;

1-[2-(4-isobutylphenyl)-2-oxoethyl]-4-(3-trifluoromethylphenyl)-1,2,3,6-tetrahydropyridine;

1-[2-(4-benzylphenyl)-2-oxoethyl]-4-(3-trifluoromethylphenyl)-1,2,3,6-tetrahydropyridine;

1-[2-(4-cyclohexylphenyl)-2-oxoethyl]-4-(3-trifluoromethylphenyl)-1,2,3,6-tetrahydropyridine;

1-[2-(4'-fluorobiphenyl-4-yl)-2-oxoethyl]-4-(3-trifluoromethylphenyl)-1,2,3,6-tetrahydropyridine;

1-[2-(4-n-butylphenyl)-2-oxoethyl]-4-(3-trifluoromethylphenyl)-1,2,3,6-tetrahydropyridine;

1-[2-(biphenyl-4-yl)-2-oxoethyl]-4-(3-trifluoromethylphenyl)-1,2,3,6-tetrahydropyridine;

1-[2-(4-t-butylphenyl)-2-oxoethyl]-4-(3-trifluoromethylphenyl)-1,2,3,6-tetrahydropyridine;

1-[2-(4'-trifluoromethylbiphenyl-4-yl)-2-oxoethyl]-4-(3-trifluoromethylphenyl)-1,2,3,6-tetrahydropyridine;
1-[2-(2,3'-dichlorobiphenyl-4-yl)ethyl]-4-(3-trifluoromethylphenyl)-1,2,3,6-tetrahydropyridine;
1-[2-(3-chlorobiphenyl-4-yl)ethyl]-4-(3-trifluoromethylphenyl)-1,2,3,6-tetrahydropyridine;
1-[2-(3',5'-dichlorobiphenyl-4-yl)ethyl]-4-(3-trifluoromethylphenyl)-1,2,3,6-tetrahydropyridine;
1-[2-(2',4'-dichlorobiphenyl-4-yl)ethyl]-4-(3-trifluoromethylphenyl)-1,2,3,6-tetrahydropyridine;
1-[2-(2-chlorobiphenyl-4-yl)ethyl]-4-(3-trifluoromethylphenyl)-1,2,3,6-tetrahydropyridine;
1-[2-(3'-chlorobiphenyl-4-yl)-2-methylpropyl]-4-(3-trifluoromethylphenyl)-1,2,3,6-tetrahydropyridine;
1-[2-(2-fluorobiphenyl-4-yl)propyl]-4-(3-trifluoromethylphenyl)-1,2,3,6-tetrahydropyridine;
1-[2-(4-methoxybiphenyl-3-yl)ethyl]-4-(3-trifluoromethylphenyl)-1,2,3,6-tetrahydropyridine;
1-[2-(4'-methoxybiphenyl-4-yl)ethyl]-4-(3-trifluoromethylphenyl)-1,2,3,6-tetrahydropyridine;
1-[2-(4'-hydroxybiphenyl-4-yl)ethyl]-4-(3-trifluoromethylphenyl)-1,2,3,6-tetrahydropyridine;
1-[2-(4'-ethoxycarbonylbutoxybiphenyl-4-yl)ethyl]-4-(3-trifluoromethylphenyl)-1,2,3,6-tetrahydropyridine;
1-[2-(biphenyl-3-yl)ethyl]-4-(3-trifluoromethylphenyl)-1,2,3,6-tetrahydropyridine;
1-[2-(3'-chloro-4'-fluorobiphenyl-4-yl)ethyl]-4-(3-trifluoromethylphenyl)-1,2,3,6-tetrahydropyridine;
1-[2-(2'-trifluoromethylbiphenyl-4-yl)ethyl]-4-(3-trifluoromethylphenyl)-1,2,3,6-tetrahydropyridine;
1-[2-(3,4-diisobutylphenyl)ethyl]-4-(3-trifluoromethylphenyl)-1,2,3,6-tetrahydropyridine;
1-[2-(3,4-dipropylphenyl)ethyl]-4-(3-trifluoromethylphenyl)-1,2,3,6-tetrahydropyridine;
1-[2-(4-cyclohexylphenyl)ethyl]-4-(6-chloropyrid-2-yl)-1,2,3,6-tetrahydropyridine;
1-[2-(4-isobutylphenyl)propyl]-4-(6-chloropyrid-2-yl)-1,2,3,6-tetrahydropyridine;
1-[2-(2'-trifluoromethylbiphenyl-4-yl)-2-oxoethyl]-4-(3-trifluoromethylphenyl)-1,2,3,6-tetrahydropyridine;
1-[2-(3'-trifluoromethylbiphenyl-4-yl)-2-oxoethyl]-4-(3-trifluoromethylphenyl)-1,2,3,6-tetrahydropyridine;
and their pharmaceutically acceptable salts and solvates.

1-(2-Naphth-2-ylethyl)-4-(3-trifluoromethylphenyl)-1,2,3,6-tetrahydropyridine and its pharmaceutically acceptable salts and solvates, especially its hydrochloride, are particularly preferred compounds for the use according to the present invention.

The compounds of formula (I) in which Z' and Z" are hydrogen are prepared as described in WO 97/01536.

The compounds of formula (I) in which one of Z' and Z" is hydrogen and the other is a hydroxyl, and the compounds in which Z' and Z" together are an oxo group, can be prepared as described in WO 93/11107.

The compounds of formula (I) in which Z" is hydrogen and Z and Z' are each independently an unsubstituted or mono-, di- or tri-substituted phenyl group are prepared by the following process:

(a) an aryl-1,2,3,6-tetrahydropyridine of formula (II):

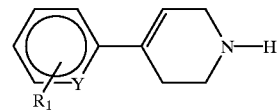

(II)

in which Y and $R_1$ are as defined above, is reacted with an acid of formula (III):

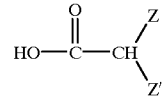

(III)

in which Z and Z' are as defined above, or one of its functional derivatives, (b) the intermediate carbonyl of formula (IV):

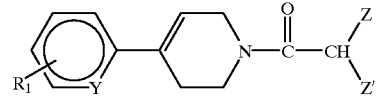

(IV)

is reduced and (c) the resulting compound of formula (I) is isolated and optionally converted to one of its salts or solvates.

The reaction of step (a) can be conveniently carried out in an organic solvent at a temperature between −10° C. and the reflux temperature of the reaction mixture; the reaction is preferably carried out at low temperature.

The reaction solvent used is preferably a halogenated solvent such as methylene chloride, dichloroethane, 1,1,1-trichloroethane, chloroform or the like, or an alcohol such as methanol or ethanol, but it is also possible to use other organic solvents compatible with the reactants employed, for example dioxane, tetrahydrofuran or a hydrocarbon such as hexane.

The reaction can be conveniently carried out in the presence of a proton acceptor, for example an alkali metal carbonate or a tertiary amine. As the appropriate functional derivative of the acid of formula (III), it is possible to use the free acid, which may be activated (for example with BOP), the anhydride, a mixed anhydride, an activated ester or an acid halide, preferably the chloride or bromide. Among the activated esters, the p-nitrophenyl ester is particularly preferred, but the methoxyphenyl, trityl, benzhydryl and similar esters are also convenient.

The reduction of step (b) can be conveniently carried out with appropriate reducing agents such as aluminum hydrides or lithium aluminum hydride, in an inert organic solvent, at a temperature between 0° C. and the reflux temperature of the reaction mixture, by the customary techniques. "Inert organic solvent" is understood as meaning a solvent which does not interfere with the reaction. Examples of such solvents are ethers such as diethyl ether, tetrahydrofuran, dioxane or 1,2-dimethoxyethane.

The compound of formula (I) obtained is isolated by the customary techniques and optionally converted to one of its acid addition salts or, if an acid group is present, the amphoteric character of the compound permits separation of the salts with either acids or bases.

The starting amines of formula (II) in which Y is CH are known compounds or they can be prepared by processes analogous to those used for preparing the known compounds.

The starting amines of formula (II) in which Y is N can be prepared by reacting the appropriate 2-halogenopyridine of formula (p):

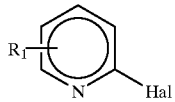

(p)

in which $R_1$ is as defined above and Hal is a halogen atom, with a 1,2,3,6-tetra-hydropyridine of formula (q):

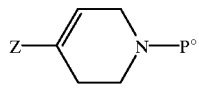

(q)

in which P° is a protecting group, for example the benzyl group, and Z is a substituent which permits nucleophilic substitution of the pyridine halogen. Examples of such substituents are trialkylstannanes, like tributylstannane, or Grignard compounds.

The 1,2,3,6-tetrahydropyridine is then deprotected by cleaving the protecting group under suitable conditions.

The acids of formula (III) can be prepared by a Wittig reaction in which:

an appropriate benzophenone of formula (r):

(r)

in which Z and Z' are as defined above, is reacted with trimethylsulfoxonium iodide/$BF_3$-$Et_2O$ and the intermediate aldehyde of formula (w):

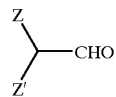

(w)

is oxidized by the method described in J. Am. Chem. Soc., 1990, 112(18), 6690–6695, to give the corresponding acid.

In another procedure, the compounds of formula (I) in which Z" is hydrogen can also be prepared by reacting an aryl-1,2,3,6-tetrahydropyridine of formula (II):

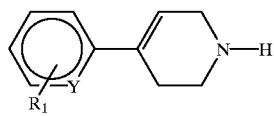

(II)

in which $R_1$ and Y are as defined above, with an aldehyde of formula (w) above, in the presence of a reducing agent such as sodium cyanoborohydride, by the known techniques.

The compounds of formula (I) in which $R_1$ is m-trifluoromethyl, Y is CH, Z' and Z" are hydrogen and Z is a naphthyl group substituted by one or two alkoxy groups or by a methylenedioxy group are prepared as described in EP 0 458 697.

1-(2-Naphth-2-ylethyl)-4-(3-trifluoromethylphenyl)-1,2,3,6-tetrahydropyridine and its pharmaceutically acceptable salts and solvates, especially the hydrochloride, can be prepared according to EP 0 101 381.

In an advantageous method, 2-(2-bromoethyl)naphthalene is reacted with 4-(3-trifluoromethylphenyl)-1,2,3,6-tetrahydropyridine and, preferably, 1-(2-naphth-2-ylethyl)-4-(3-trifluoromethylphenyl)-1,2,3,6-tetrahydropyridine hydrochloride is isolated; this is subsequently crystallized from an ethanol/water mixture by heating and cooling to 5° C. at a rate of 10° C./hour and with a stirrer speed of 400 rpm to give a mixture of two crystalline forms in a ratio of about 66/34.

1-(2-Naphth-2-ylethyl)-4-(3-trifluoromethylphenyl)-1,2,3,6-tetrahydropyridine hydrochloride is preferably used in microparticulate form, for example in an essentially amorphous form obtained by atomization or in a microcrystalline form obtained by micronization.

The activity of the compounds of formula (I) was investigated in the model of experimental allergic encephalitis (EAE) induced in Lewis rats by the intraplantar administration of myelin basic protein (MBP) (fragment 68–84) in a Freund's complete adjuvant (FCA) enriched in Mycobacterium tuberculosis, according to the protocol published by Martin and Near (Journal of Neuroimmunology, 1995, 241–245).

EAE is an inflammatory autoimmune disease of the central nervous system which presents demyelinating lesions reminiscent of human multiple sclerosis.

In this experimental model, representative compounds according to the invention, administered orally from day zero of induction of the disease, very significantly alleviate the disease as measured both by the variations in weight of the animals (the diseased animals present a large weight loss) and by the severity of the pathological condition (the diseased animals present paralysis of the back paws). The weight loss of the treated animals, especially those treated with 1-(2-naphth-2-ylethyl)-4-(3-trifluoromethylphenyl)-1,2,3,6-tetrahydropyridine hydrochloride, is significantly lower than that of the animals treated with the vehicle only. Likewise, the disease is statistically less severe in the groups of animals treated with 1-(2-naphth-2-ylethyl)-4-(3-trifluoromethylphenyl)-1,2,3,6-tetrahydropyridine hydrochloride.

Another recognized major event in multiple sclerosis is the loss of integrity of the blood-brain barrier under attack of the immune system. This pathological effect is also demonstrated in the EAE model.

It was verified that the degradation of the blood-brain barrier is substantially reduced, or even non-existent (the barrier presenting no permeability anomaly), in the animals treated with representative compounds of the invention, compared with the control animals.

The results of these studies show that the compounds of formula (I), especially 1-(2-naphth-2-ylethyl)-4-(3-trifluoromethylphenyl)-1,2,3,6-tetrahydropyridine and its pharmaceutically acceptable salts and solvates, have a favorable action in this pathological condition of neurological dysfunction and can thus be clinically applied in the treatment of diseases which cause demyelinating lesions, such as multiple sclerosis.

The compounds of formula (I) and their pharmaceutically acceptable salts and solvates are preferably administered orally.

In the pharmaceutical compositions of the present invention for oral administration, the active principle can be administered to animals and humans in unit forms of administration, mixed with conventional pharmaceutical carriers, for the treatment of the above-mentioned complaints. The appropriate unit forms of administration include for example tablets, which may be divisible, gelatin capsules, powders, granules and solutions or suspensions to be taken orally.

When a solid composition is prepared in the form of tablets, the main active ingredient is mixed with a pharmaceutical vehicle such as gelatin, starch, lactose, magnesium stearate, talcum, gum arabic or the like. The tablets can be coated with sucrose or other appropriate substances, or else they can be treated so as to have a sustained or delayed activity and so as to release a predetermined amount of active principle continuously.

A preparation in the form of gelatin capsules is obtained by mixing the active ingredient with a diluent and pouring the resulting mixture into soft or hard gelatin capsules.

A preparation in the form of a syrup or elixir can contain the active ingredient together with a sweetener, which is preferably calorie-free, methylparaben and propylparaben as antiseptics, a flavoring and an appropriate color.

The water-dispersible powders or granules can contain the active ingredient mixed with dispersants or wetting agents or with suspending agents such as polyvinylpyrrolidone, as well as with sweeteners or taste correctors.

The active principle can also be formulated as microcapsules, optionally with one or more carriers or additives.

In the pharmaceutical compositions according to the present invention, the active principle can also be in the form of an inclusion complex in cyclodextrins, their ethers or their esters.

The amount of active principle to be administered depends, as always, on how advanced the disease is and on the patient's age and weight. Nevertheless the unit doses generally comprise from 0.1 to 100 mg, preferably from 0.25 to 50 mg and particularly preferably from 0.5 to 20 mg of active principle.

The preferred compound for the use according to the present invention, i.e. 1-(2-naphth-2-ylethyl)-4-(3-trifluoromethylphenyl)-1,2,3,6-tetrahydropyridine hydrochloride in microparticulate form, is used in unit doses of 0.5 to 10 mg, advantageously of 1 to 5 and preferably of 1 to 3 mg, for example 1, 1.5, 2, 2.5 or 3 mg, of active principle. These unit doses are normally administered one or more times a day, preferably one to three times a day, the overall dose in humans varying between 0.5 and 50 mg per day, for example from 1 to 20 mg per day and advantageously from 2 to 10 mg per day.

According to another of its aspects, the present invention relates to a synergistic association comprising a compound of formula (I), or one of its pharmaceutically acceptable salts or solvates, and at least one compound selected from immunosuppressants such as interferon β-1b; adrenocorticotropic hormone; glucocorticoids such as prednisone or methylprednisolone; and interleukin-1 inhibitors.

More particularly, the invention relates to an association comprising a compound of formula (I), or one of its pharmaceutically acceptable salts or solvates, and at least one compound selected from roquinimex (1,2-dihydro-4-hydroxy-N,1-dimethyl-2-oxo-3-quinolinecarboxanilide), myloran (a product from Autoimmune containing bovine myelin), antegren (a monoclonal human antibody from Elan/Athena Neurosciences) and recombinant interferon β-1a.

Other possible associations are those consisting of a compound of formula (I), or one of its pharmaceutically acceptable salts or solvates, and a potassium channel blocker, for example fampridine (4-aminopyridine).

According to another aspect, the present invention relates to a method of treating diseases which cause demyelination, comprising the administration, to a subject in need thereof, of an effective amount of a compound of formula (I) or one of its pharmaceutically acceptable salts or solvates.

According to another aspect, the present invention relates to a method of treating diseases which cause demyelination, comprising the administration, to a subject in need thereof, of an effective amount of an association comprising a compound of formula (I), or one of its pharmaceutically acceptable salts or solvates, and at least one compound selected from immunosuppressants such as interferon β-1b; adrenocorticotropic hormone; glucocorticoids such as prednisone or methylprednisolone; and interleukin-1 inhibitors.

The Examples which follow illustrate the invention more clearly without however implying a limitation.

EXAMPLE 1

1-(2,2-Diphenylethyl)-4-(3-trifluoromethylphenyl)-1,2,3,6-tetrahydropyridine and its hydrochloride 1a/1-(α, α-Diphenylacetyl)-4-(3-trifluoromethylphenyl)-1,2,3,6-tetrahydropyridine 8 g of α,α-diphenylacetyl chloride in 50 ml of methylene chloride are added dropwise at a temperature of 0/+5° C. to a mixture of 8 g (0.035 mol) of 4-(3-trifluoromethylphenyl)-1,2,3,6-tetrahydropyridine, 50 ml of methylene chloride and 4.96 ml of triethylamine. The resulting mixture is stirred for one hour at room temperature, the solvent is evaporated off under reduced pressure and the residue is taken up with ethyl ether and washed with 0.2 M aqueous hydrochloric acid solution, with water, with aqueous sodium carbonate solution and again with water. It is dried over sodium sulfate and the solvent is evaporated off under reduced pressure to give 5 g of the title compound.

1b/1-(2,2-Diphenylethyl)-4-(3-trifluoromethylphenyl)-1,2,3,6-tetrahydropyridine and its hydrochloride A solution of 5 g (0.012 mol) of the product of the previous step in 50 ml of ethyl ether is added dropwise at 25° C. to a mixture of 0.7 g of lithium aluminum hydride and 10 ml of ethyl ether. The resulting mixture is stirred at room temperature for one hour and 5 ml of water are added dropwise. The two phases are separated, the organic phase is dried over sodium sulfate and the solvent is evaporated off under reduced pressure to give 1-( 2,2-diphenylethyl)-4-(3-trifluoromethylphenyl)-1,2,3,6-tetrahydropyridine. The hydrochloride is prepared using a saturated solution of hydrochloric acid in ethyl ether. It is crystallized from 150 ml of ethyl acetate. M.p. (hydrochloride)=207–210° C.

EXAMPLE 2

1-[2,2-(4,4'-Dichlorodiphenyl)ethyl]-4-(3-trifluoromethylphenyl)-1,2,3,6-tetrahydropyridine and its oxalate 2a/α,α-(4,4 '-Dichlorodiphenyl)acetaldehyde 0.75 g (0.025 mol) of sodium hydride as an 80% dispersion in oil is added in portions to a mixture of 5.5 g (0.025 mol) of trimethylsulfoxonium iodide and 10 ml of anhydrous tetrahydrofuran. The resulting mixture is heated at 55° C. for 6 hours and 6 g (0.025 mol) of 4,4'-dichlorobenzophenone in 10 ml of anhydrous tetrahydrofuran are added. The mixture is stirred at 55° C. overnight, poured into water and extracted with ethyl ether, the organic phase is dried over sodium sulfate and the solvent is evaporated off under reduced pressure. The residue is dissolved in 32 ml of toluene, and 3 ml of BF$_3$-Et$_2$O are added. The mixture is stirred for 2 minutes and then left to stand for 3 minutes. It is washed twice with aqueous sodium bicarbonate solution, the organic phase is dried over sodium sulfate and the solvent is evaporated off under reduced pressure to give an oil, which is purified by chromatography on a silica gel column using a 9/1 hexane/ethyl acetate mixture as the eluent to give the title compound.

2b/1-[2,2-(4,4'-Dichlorodiphenyl)ethyl]-4-(3-trifluoromethylphenyl)-1,2,3,6-tetrahydropyridine and its oxalate 1.3 g (0.0045 mol) of the product of the previous step, 1.2 g (0.0053 mol) of 4-(3-trifluoromethylphenyl)-1,2,3,6-tetrahydropyridine, 21 ml of methanol, 0.8 ml of glacial acetic acid and 0.5 g of anhydrous sodium acetate are mixed at a temperature of 0/+5° C. 0.76 g (0.0121 mol) of sodium cyanoborohydride is added to the mixture at the same temperature and the resulting mixture is stirred at low temperature for 1.5 hours and then at room temperature overnight. 5 ml of concentrated hydrochloric acid are added dropwise, the mixture is stirred for 10 minutes, the methanol is evaporated off and the residue is taken up with a mixture of ethyl acetate and dilute aqueous $NH_4OH$ solution. The two phases are separated, the organic phase is dried over sodium sulfate and the solvent is evaporated off under reduced pressure to give an oil, which is purified by chromatography on a silica gel column using a 9/1 hexane/ethyl acetate mixture as the eluent to give the title compound in the form of the base. The oxalate is prepared with oxalic acid in isopropanol. M.p. (oxalate)=187–189° C.

EXAMPLE 3

1-[2,2-(3,3'-Bistrifluoromethyldiphenyl)ethyl]-4-(3-trifluoromethylphenyl)-1,2,3,6-tetrahydropyridine and its oxalate 3a/α,α-(3,3'-Bistrifluoromethyldiphenyl)acetaldehyde The title compound is obtained by following the procedure described in Example 2a/ but using 3,3'-bistrifluoromethylbenzophenone.

3b/1-[2,2-(3,3 ' Bistrifluoromethyldiphenyl)ethyl]-4-(3-trifluoromethylphenyl)-1,2,3,6-tetrahydropyridine and its oxalate The title compounds are obtained by following the procedure described in Example 2b/ but using the product of the previous step instead of the α,α-(4,4'-dichlorodiphenyl) acetaldehyde. M.p. (oxalate)=194–196° C.

EXAMPLE 4

1-[2,2-(4,4'-Dimethoxydiphenyl)ethyl]-4-(3-trifluoromethylphenyl)-1,2,3,6-tetrahydropyridine and its hydrochloride 4a/α,α-(4,4'-Dimethoxydiphenyl)acetaldehyde The title compound is obtained by following the procedure described in Example 2a/ but using 4,4'-dimethoxybenzophenone.

4b/1-[2,2-(4,4 '-Dimethoxydiphenyl)ethyl]-4-(3-trifluoromethylphenyl)-1,2,3,6-tetrahydropyridine and its hydrochloride The title compounds are obtained by following the procedure described in Example 2b/ but using the product of the previous step instead of the α,α-(4,4'-dichlorodiphenyl) acetaldehyde. M.p. (hydrochloride)=214–216° C.

EXAMPLE 5

1-[2-(4-Fluorophenyl)-2-phenylethyl]-4-(3-trifluoromethylphenyl)-1,2,3,6-tetrahydropyridine and its hydrochloride 5a/α-4-Fluorophenyl-α-phenylacetaldehyde The title compound is obtained by following the procedure described in Example 2a/ but using 4-fluorobenzophenone.

5b/1-[2-(4-Fluorophenyl)-2-phenylethyl]-4-(3-trifluoromethylphenyl)-1,2,3, 6-tetrahydropyridine and its hydrochloride The title compounds are obtained by following the procedure described in Example 2b/ but using the product of the previous step instead of the α,α-( 4,4'-dichlorodiphenyl) acetaldehyde. M.p. (hydrochloride)=206–208° C.

EXAMPLE 6

1-(3,3-Diphenylpropyl)-4-(3-trifluoromethylphenyl)-1,2,3,6-tetrahydro-pyridine and its hydrochloride The title compounds are obtained by following the procedure described in Example 1b/ but using commercial 3,3-diphenylpropionic acid (Aldrich, reference D21, 165–6) instead of the 2,2-diphenylacetic acid. M.p. (hydrochloride)=176–178° C.

EXAMPLE 7

1-[2,2-(4,4'-Dichlorodiphenyl)ethyl]-4-(6-chloropyrid-2-yl)-1,2,3,6-tetrahydropyridine and its hydrochloride The title compounds are obtained by following the procedure described in Example 2b/ but using 4-(6-chloropyrid-2-yl)-1,2,3,6-tetrahydropyridine instead of the 4-(3-trifluoromethylphenyl)-1,2,3,6-tetrahydropyridine. M.p. (hydrochloride)=230–32° C.

EXAMPLE 8

1-[2-(3,4-Diethylphenyl)ethyl]-4-(3-trifluoromethylphenyl)-1,2,3,6-tetrahydropyridine hydrochloride 8a/1-Bromo-2-(3,4-diethylphenyl)ethane A mixture of 4.4 g (0.033 mol) of 3,4-diethylbenzene, 50 ml of methylene chloride and 8.8 g (0.044 mol) of bromoacetyl bromide is cooled to 0–5° C. and 5.0 g (0.037 mol) of aluminum trichloride are added. The resulting mixture is stirred at 0–5° C. for one hour and then left at room temperature overnight. It is poured into a water/ice mixture and extracted with methylene chloride, the organic phase is dried over sodium sulfate and the solvent is evaporated off under reduced pressure. 2.9 g (0.011 mol) of the resulting oil are mixed with 6 ml (0.079 mol) of trifluoroacetic acid and 6.7 ml (0.057 mol) of triethylsilane and the mixture is heated at 80° C. for 4 hours. Saturated aqueous sodium bicarbonate solution is then added until the pH is basic, the mixture is extracted with ethyl ether, the organic phase is dried over sodium sulfate and the solvent is evaporated off under reduced pressure. The resulting crude oil is purified by chromatography on a silica gel column using cyclohexane as the eluent to give the title compound.

8b/1-[2-(3,4-Diethylphenyl)ethyl]-4-(3-trifluoromethylphenyl)-1,2,3,6-tetra-hydropyridine hydrochloride A mixture of 2.6 g (0.001 mol) of 4-(3-trifluoromethylphenyl)1,2,3,6-tetrahydropyridine, 60 ml of butanol, 4.1 g (0.025 mol) of anhydrous potassium carbonate chips and 2.6 g (0.00113 mol) of the product of the previous step is refluxed for 5 hours. The solvent is evaporated off under reduced pressure, the residue is taken up with ethyl acetate and washed with water, the organic phase is dried over sodium sulfate and the solvent is evaporated off under reduced pressure. The hydrochloride of the resulting oil is prepared by treatment with a saturated solution of hydrochloric acid in isopropanol to give 1.6 g of the title compound. M.p.=220–222° C.

EXAMPLE 9

1-[2-(3-Methyl-4-pentylphenyl)ethyl]-4-(3-trifluoromethylphenyl)-1,2,3,6-tetrahydropyridine and 1-[2-(4-methyl-3-pentylphenyl)ethyl]-4-(3-trifluoromethylphenyl)-1,2,3,6-tetrahydropyridine and their oxalates 9a/1-Methyl-2-pentylbenzene 4.7 g (0.035 mol) of phthalaldehyde are added dropwise to 50 ml (0.1 mol) of a 2 M solution of n-butylmagnesium chloride in THF under a nitrogen atmosphere. The mixture warms up spontaneously to 40–45° C. It is stirred at room temperature for one hour and poured into saturated ammonium chloride solution. The resulting mixture is extracted with ethyl ether and washed with water, the organic phase is dried over sodium sulfate and the solvent is evaporated off under reduced pressure. The resulting oil is purified by chromatography on a silica gel column using a 7/3 cyclohexane/ethyl acetate mixture as the eluent. The product of higher Rf is isolated to give 2.0 g of an oil. The crude reaction product is dissolved in 25 ml of ethanol, and 1 ml of concentrated sulfuric acid and 0.15 g of 10% Pd/C are added. The mixture is hydrogenated at room temperature for 7 hours. The catalyst is filtered off, the solvent is evaporated off under reduced pressure and the residue is taken up with ethyl acetate. The mixture is washed with aqueous sodium bicarbonate solution and dried and the solvent is evaporated off under reduced pressure to give 1.35 g of the title product.

9b/1-Bromo-2-(3-methyl-4-pentylphenyl)ethane and 1-bromo-2-(4-methyl-3-pentylphenyl)ethane A mixture of 1.17 g (0.0054 mol) of the product of the previous step and 0.62 ml (0.0072 mol) of bromoacetyl bromide is cooled to 0–5° C. and 0.81 g (0.006 mol) of aluminum trichloride is added. The resulting mixture is stirred at 0–5° C. for one hour and then at room temperature for 4 hours. It is poured onto ice, the two phases are separated, the organic phase is washed with water and dried and the solvent is evaporated off under reduced pressure. The residue is dissolved in 2.9 ml of trifluoroacetic acid, 3.1 ml (0.0267 mol) of triethylsilane are added and the mixture is heated at 80° C. for 5 hours. It is poured into aqueous sodium bicarbonate solution and extracted with ethyl ether. The organic phase is washed with water and dried over sodium sulfate to give a mixture of the title compounds.

9c/1-[2-(3-Methyl-4-pentylphenyl)ethyl]-4-(3-trifluoromethylphenyl)-1,2,3,6-tetrahydropyridine and 1-[2-(4-methyl-3-pentylphenyl)ethyl]-4-(3-trifluoromethylphenyl)-1,2,3,6-tetrahydropyridine and their oxalates A mixture of 0.7 g (0.0031 mol) of 4-(3-trifluoromethylphenyl)-1,2,3,6-tetrahydropyridine, 16 ml of butanol, 0.9 g (0.0065 mol) of anhydrous potassium carbonate chips and the product obtained in the previous step (theoretical amount=0.0054 mol) is refluxed for 6 hours. The solvent is evaporated off under reduced pressure, the residue is taken up with ethyl acetate and washed with water, the organic phase is dried over sodium sulfate and the solvent is evaporated off under reduced pressure. The resulting oil is purified by chromatography on a silica gel column using a 7/3 cyclohexane/ethyl acetate mixture as the eluent. Two products of similar Rf are isolated. The product of higher Rf corresponds to 1-[2-(3-methyl-4-pentylphenyl)ethyl]-4-(3-trifluoromethylphenyl)-1,2,3,6-tetrahydropyridine. The oxalate is prepared in acetone to give 0.12 g of product. M.p.=140–143° C. The product of lower Rf corresponds to the isomer 1-[2-(4-methyl-3-pentylphenyl)ethyl]-4-(3-trifluoromethylphenyl)-1,2,3,6-tetrahydropyridine. The oxalate is prepared in acetone. The product is crystallized from acetone to give 0.08 g of product. M.p.=167–169° C.

EXAMPLE 10

1-[2-(3,4-Diethylphenyl)ethyl]-4-(6-chloropyrid-2-yl)-1,2,3,6-tetrahydropyridine hydrochloride 10a/(1-Benzyl-1,2,3,6-tetrahydropyrid-4-yl)tributylstannane A mixture of 15.85 g (0.0837 mol) of 1-benzyl-4-piperidone in 140 ml of anhydrous dimethoxyethane and 25 g (0.0837 mol) of trisilidrazine in 140 ml of anhydrous dimethoxyethane is stirred at room temperature for 3 hours. The solvent is evaporated off under reduced pressure. The residue is taken up with 420 ml of anhydrous hexane, and 420 ml of anhydrous tetramethylethylenediamine are added. The mixture is cooled to −78° C. and 156 ml of n-butyllithium (0.25 mol) (1.6 M solution in hexane) are added dropwise. After about 30 minutes, the temperature is allowed to rise to 0° C. and the reaction mixture is stirred for 15 minutes. 45 ml (0.167 mol) of tributylstannane chloride are then added. After 1 hour, a water/ice mixture is added with extreme caution. The mixture is extracted with ethyl ether, the organic phase is washed with water and dried over sodium sulfate and the solvent is evaporated off under reduced pressure to give 70 g of crude product, which is purified by chromatography on a silica gel column using a 95/5 cyclohexane/ethyl acetate mixture as the eluent to give the title compound in the form of an oil.

$^1$H NMR (CDCl$_3$) δ (ppm): 0.84 (9H; m: CH$_3$); 1.19–1.58 (18H; m: chain CH$_2$); 2.31 (2H; m); 2.53 (2H; m); 3.02 (2H; m); 3.56 (2H; s: benzylic methylene); 5.76 (1H; m*); 7.18–7.41 (5H; m: arom.) * satellite bands: $^3J_{cis}$($^1$H—$^{117}$Sn) and $^3J_{cis}$($^1$H—$^{119}$Sn)

10b/1-Benzyl-4-(6-chloropyrid-2-yl)-1,2,3,6-tetrahydropyridine 18.5 g (0.04 mol) of the compound of the previous step are dissolved in 200 ml of anhydrous dimethylformamide under a nitrogen atmosphere. 11.8 g (0.08 mol) of 2,6-dichloropyridine, 0.64 g of Pd$^{II}$(Ph$_3$P)$_2$Cl$_2$, 4.38 g (0.04 mol) of tetramethylammonium chloride and 2.76 g (0.02 mol) of potassium carbonate are added to the solution. The mixture is heated at 110° C. for 6 hours and then poured into 100 ml of 5% sulfuric acid solution. The resulting mixture is extracted with ethyl ether, ammonium hydroxide is added to the aqueous phase until the pH is basic, and the mixture is extracted with ethyl acetate. The combined organic phases are dried over sodium sulfate and the solvent is evaporated off under reduced pressure. The residue is purified by chromatography on a silica gel column using a 1/1 cyclohexane/ethyl acetate mixture as the eluent to give the title compound.

M.p.=100–102° C.

10c/4-(6-Chloropyrid-2-yl)-1,2,3,6-tetrahydropyridine hydrochloride

A solution of 7.0 g (0.024 mol) of the compound of the previous step in 110 ml of dichloroethane is cooled to 0–5° C. and 5.8 ml (0.054 mol) of chloroethyl chloroformate are added. The mixture is stirred for 5 minutes and then refluxed for 1.5 hours. The solvent is evaporated off under reduced pressure and the residue is taken up with 100 ml of methanol and refluxed for 1 hour. The solvent is evaporated off, the residue is taken up with isopropanol and the solid is filtered off to give the title compound, which is crystallized from 90% ethanol. M.p.=305–307° C.

10d/1-[2-(3,4-Diethylphenyl)ethyl]-4-(6-chloropyrid-2-yl)-1,2,3,6-tetrahydropyridine hydrochloride The title compound is obtained by following the procedure described in Example 8b/ but using the product of the previous step instead of the 4-(3-trifluoromethylphenyl)-1,2,3,6-tetrahydropyridine. M.p.=234–236° C.

EXAMPLES 11–20

The compounds below are obtained by following the procedure described in Example 9 but using the appropriate magnesium halide:

1-[2-(3-ethyl-4-methylphenyl)ethyl]-4-(3-trifluoromethylphenyl)-1,2,3,6-tetrahydropyridine-Ex. 11

1-[2-(4-ethyl-3-methylphenyl)ethyl]-4-(3-trifluoromethylphenyl)-1,2,3,6-tetrahydropyridine-Ex. 12

1-[2-(3-ethyl-4-propylphenyl)ethyl]-4-(3-trifluoromethylphenyl)-1,2,3,6-tetrahydropyridine-Ex. 13

1-[2-(4-ethyl-3-propylphenyl)ethyl]-4-(3-trifluoromethylphenyl)-1,2,3,6-tetrahydropyridine-Ex. 14

1-[2-(3-butyl4-methylphenyl)ethyl]-4-(3-trifluoromethylphenyl)-1,2,3,6-tetrahydropyridine-Ex. 15

1-[2-(4-butyl-3-methylphenyl)ethyl]-4-(3-trifluoromethylphenyl)-1,2,3,6-tetrahydropyridine-Ex. 16

1-[2-(3-isobutyl-4-methylphenyl)ethyl]-4-(3-trifluoromethylphenyl)-1,2,3,6-tetrahydropyridine-Ex. 17

1-[2-(4-isobutyl-3-methylphenyl)ethyl]-4-(3-trifluoromethylphenyl)-1,2,3,6-tetrahydropyridine-Ex. 18

1-[2-(3-isobutyl-4-ethylphenyl)ethyl]-4-(3-trifluoromethylphenyl)-1,2,3,6-tetrahydropyridine-Ex. 19

1-[2-(4-isobutyl-3-ethylphenyl)ethyl]-4-(3-trifluoromethylphenyl)-1,2,3,6-tetrahydropyridine-Ex. 20

EXAMPLE 21

1-[2-(6-Methylbiphenyl-3-yl)ethyl]-4-(3-trifluoromethylphenyl)-1,2,3,6-tetrahydropyridine The title compound is obtained by following the procedure described in Example 9 but using phenyllithium instead of the n-butylmagnesium chloride.

EXAMPLE 22

1-[2-(3'-Chlorobiphenyl-4-yl)-2-oxoethyl]-4-(3-trifluoromethylphenyl)-1,2,3,6-tetrahydropyridine hydrochloride 22a/1-Bromo-2-(3'-chlorobiphenyl-4-yl)ethanone A mixture of 5 g (0.026 mol) of 3-chlorobiphenyl, 50 ml of methylene chloride and 6.95 g (0.034 mol) of bromoacetyl bromide is cooled to 0–5° C. and 4 g (0.030 mol) of aluminum trichloride are added. The resulting mixture is stirred for 1 hour at 5° C. and then for 4 hours at room temperature. It is poured into a water/ice mixture and extracted with methylene chloride and the organic phase is washed with 1 N HCl solution, dried over sodium sulfate and evaporated under reduced pressure to give 4.5 g of the title compound. M.p.=63–65° C.

22b/1-[2-(3'-Chlorobiphenyl-4-yl)-2-oxoethyl]-4-(3-trifluoromethylphenyl)-1,2,3,6-tetrahydropyridine hydrochloride A mixture of 0.4 g (0.013 mol) of the product of the previous step, 2.95 g (0.013 mol) of 4-(3-trifluoromethylphenyl)-1,2,3,6-tetrahydropyridine, 80 ml of ethanol and 2.32 g (0.0167 mol) of anhydrous potassium carbonate chips is refluxed for 1 hour. The salts are filtered off and the solution is acidified by the addition of a saturated solution of hydrochloric acid in ethanol. It is concentrated under reduced pressure to about 40 ml and left to stand overnight at 5° C. The precipitate is filtered off and washed with water and then with isopropanol to give 4.9 g of the title compound. M.p.=217–220° C.

EXAMPLE 23

1-[2-(2'-Chlorobiphenyl-4-yl)-2-oxoethyl]-4-(3-trifluoromethylphenyl)-1,2,3,6-tetrahydropyridine hydrochloride The title compound is obtained by following the procedure described in Example 22 but using 2-chlorobiphenyl instead of the 3-chlorobiphenyl.

M.p.=200–202° C. (crystallized from isopropanol).

EXAMPLE 24

1-[2-(4'-Chlorobiphenyl-4-yl)-2-oxoethyl]-4-(3-trifluoromethylphenyl)-1,2,3,6-tetrahydropyridine hydrochloride The title compound is obtained by following the procedure described in Example 22 but using 4-chlorobiphenyl instead of the 3-chlorobiphenyl.

M.p.=210–215° C.

EXAMPLE 25

1-[2-(4-Isobutylphenyl)-2-oxoethyl]-4-(3-trifluoromethylphenyl)-1,2,3,6-tetrahydropyridine hydrochloride The title compound is obtained by following the procedure described in Example 22 but using 4-isobutylbenzene instead of the 3-chlorobiphenyl.

M.p.=224–228° C. (crystallized from isopropanol).

EXAMPLE 26

1-[2-(4-Phenoxyphenyl)-2-oxoethyl]-4-(3-trifluoromethylphenyl)-1,2,3,6-tetrahydropyridine hydrochloride The title compound is obtained by following the procedure described in Example 22 but using diphenyl ether instead of the 3-chlorobiphenyl. M.p.=205–210° C.

EXAMPLE 27

1-[2-(4–Cyclohexylphenyl)-2-oxoethyl]-4-(3-trifluoromethylphenyl)-1,2,3,6-tetrahydropyridine hydrochloride The title compound is obtained by following the procedure described in Example 22 but using cyclohexylbenzene instead of the 3-chlorobiphenyl.

M.p.=209–213° C. (crystallized from isopropanol).

EXAMPLE 28

1-[2-(4'-Fluorobiphenyl-4-yl)-2-oxoethyl]-4-(3-trifluoromethylphenyl)-1,2,3,6-tetrahydropyridine hydrochloride The title compound is obtained by following the procedure described in Example 22 but using 4-fluorobiphenyl instead of the 3-chlorobiphenyl.

M.p.=123–125° C. (crystallized from isopropanol).

EXAMPLE 29

1-[2-(Biphenyl-4-yl)-2-oxoethyl]-4-(3-trifluoromethylphenyl)-1,2,3,6-tetrahydropyridine hydrochloride The title compound is obtained by following the procedure described in Example 22 but using biphenyl instead of the 3-chlorobiphenyl. M.p.=145–147° C. (base); m.p.=240–243° C. (hydrochloride).

EXAMPLE 30

1-[2-(4-n-Butylphenyl)-2-oxoethyl]-4-(3-trifluoromethylphenyl)- 1,2,3,6-tetrahydropyridine hydrochloride The title compound is obtained by following the procedure described in Example 22 but using 4-n-butylbenzene instead of the 3-chlorobiphenyl.

M.p.=218–221° C.

EXAMPLE 31

1-[2-(4-t-Butylphenyl)-2-oxoethyl]4-(3-trifluoromethylphenyl)-1,2,3,6-tetrahydropyridine hydrochloride The title compound is obtained by following the procedure described in Example 22 but using 4-t-butylbenzene instead of the 3-chlorobiphenyl.

M.p.=97–99° C. (base).

EXAMPLE 32

1-[2-(3,4-Diethylphenyl)-2-oxoethyl]-4-(3-trifluoromethylphenyl)-1,2,3,6-tetrahydropyridine hydrochloride The title compound is obtained by following the procedure described in Example 22 but using 3,4-diethylbenzene instead of the 3-chlorobiphenyl.

M.p.=232–234° C.

EXAMPLE 33

1-[2-(2'-Trifluoromethylbiphenyl-4-yl)-2-oxoethyl]-4-(3-trifluoromethyl-phenyl)-1,2,3,6-tetrahydropyridine hydrochloride 33a/2-(4-Bromophenyl)-2,2-dimethoxyethane A mixture of 2 g (0.01 mol) of 4-bromoacetophenone, 5.6 ml of trimethyl orthoformate, 5.6 ml of methanol and 0.67 g of Amberlite® IR 120 is refluxed for 3 hours. After cooling, it is filtered on Célite® and the filtered solution is evaporated to give 2.4 g of the title compound in the form of an oil.

33b/2,2-Dimethoxy-2-(2'-trifluoromethylbiphenyl-4-yl)ethane

A mixture of 4.9 g (14 mmol) of the product of the previous step, 2.45 g (16 mmol) of 2-trifluoromethylbenzeneboronic acid, 63 mg (0.28 mmol) of palladium acetate, 4.84 g (35 mmol) of potassium carbonate and 4.5 g (14 mmol) of tetrabutylammonium bromide in 19 ml of water is stirred at 70° C. for 1 hour. It is allowed to cool and extracted with ethyl acetate. The organic phase is dried over sodium sulfate and filtered and the solvent is evaporated off under reduced pressure to give the title compound in the form of an oil.

33c/4-(2-Trifluoromethylphenyl)acetophenone

A solution of 4 ml of trifluoroacetic acid and 4 ml of water is added at 0° C. to a solution of 4.6 g (0.0105 mol) of the product of the previous step in 4 ml of methylene chloride. The mixture is stirred at room temperature for 2 hours, poured into water and extracted with methylene chloride. The organic phase is dried and filtered and the solvent is evaporated off under reduced pressure. The crude product is purified by chromatography on a silica gel column using a 9/1 cyclohexane/ethyl acetate mixture as the eluent to give 1.97 g of the title compound.

33d/α-Bromo-4-(2-trifluoromethylphenyl)acetophenone 0.38 ml (7.5 mmol) of bromine is added dropwise at a temperature of 0° C. to a solution of 1.97 g (7.5 mmol) of the product of the previous step in 5.4 ml of methanol. The mixture is stirred at room temperature for 3 hours, the solvent is evaporated off and the residue is taken up with water and extracted with ethyl acetate. The organic phase is dried over sodium sulfate and filtered and the solvent is evaporated off under reduced pressure to give the title compound in the form of an oil.

33e/1-[2-(2' Trifluoromethylbiphenyl-4-yl)-2-oxoethyl]-4-(3-trifluoromethylphenyl)-1,2,3,6-tetrahydropyridine hydrochloride A mixture of 0.74 g (0.0028 mol) of 4-(3-trifluoromethylphenyl)-1,2,3,6-tetrahydropyridine, 14 ml of ethanol and 1.27 g (0.0092 mol) of anhydrous potassium carbonate chips is refluxed for 1 hour. A solution of 1.2 g (0.0035 mol) of the oil of the previous step in 3 ml of ethanol is added and the mixture is refluxed for 30 minutes. The salts are filtered off and the solution is acidified by the addition of 1 N aqueous hydrochloric acid solution. The solvent is evaporated off under reduced pressure, the residue is extracted with chloroform, the organic phase is dried over sodium sulfate and filtered and the solvent is evaporated off under reduced pressure. The base is freed with concentrated aqueous ammonia solution and extracted with ethyl acetate and the product is purified by chromatography on a silica gel column using an 8/2 cyclohexane/ethyl acetate mixture as the eluent to give the title compound. The hydrochloride is prepared with a saturated solution of hydrochloric acid in isopropanol. M.p.=195–197° C.

EXAMPLE 34

1-[2-(3'-Trifluoromethylbiphenyl-4-yl)-2-oxoethyl]-4-(3-trifluoromethylphenyl)-1,2,3,6-tetrahydropyridine hydrochloride The title compound is obtained by following the procedure described in Example 33 but using 3-trifluoromethylbenzeneboronic acid instead of the 2-trifluoromethylbenzeneboronic acid in step 33b/. M.p.=232–234° C.

EXAMPLE 35

1-[2-(4'-Trifluoromethylbiphenyl-4-yl)-2-oxoethyl]-4-(3-trifluoromethylphenyl)-1,2,3,6-tetrahydropyridine hydrochloride The title compound is obtained by following the procedure described in Example 33 but using 4-trifluoromethylbenzeneboronic acid instead of the 2-trifluoromethylbenzeneboronic acid in step 33b/. M.p.=245–247° C.

EXAMPLE 36

A mixture of 12.5 g of 2-(2-bromoethyl)naphthalene, 14 g of 4-(3-trifluoromethylphenyl)-1,2,3,6-tetrahydropyridine hydrochloride, 4.34 g of sodium hydroxide, 135 ml of water and 95 ml of 95% ethanol is refluxed for 5 hours and the reaction mixture is then allowed to cool to room temperature overnight. It is cooled to below 25° C. and then filtered and the product isolated in this way is washed with water and dried under vacuum at 50° C. to give 1-[2-(naphth-2-yl)ethyl]-4-(3-trifluoromethylphenyl)-1,2,3,6-tetrahydropyridine base with a yield of 90%, calculated relative to the starting 4-(3-trifluoromethylphenyl)-1,2,3,6-tetrahydropyridine hydrochloride.

EXAMPLE 37

A mixture of 19.5 g of crude 1-[2-(naphth-2-yl)ethyl]-4-(3-trifluoromethylphenyl)-1,2,3,6-tetrahydropyridine hydrochloride, 95 ml of absolute ethanol and 4.65 ml of 37% hydrochloric acid is refluxed, with stirring, until everything has dissolved, and is then allowed to cool, with continued stirring. When the first crystals start to form (at about 63° C.), stirring is stopped and the reaction mixture is kept at 0–5° C. overnight. After filtration, the product is made into a paste twice with 30 ml of absolute ethanol and then dried overnight at 40° C. under vacuum.

12.8 g of form I of 1-[2-(naphth-2-yl)ethyl]-4-(3-trifluoromethylphenyl)-1,2,3,6-tetrahydropyridine hydrochloride were obtained under these conditions.

In differential scanning calorimetry, the form I obtained in this preparation showed:

a solid-solid transition temperature of 148–149° C.

an enthalpy of transition of 26.4 J/g.

EXAMPLE 38

In a METTLER RC1 calorimetric reactor equipped with an impeller of diameter 8 cm, a mixture of 70 g of crude 1-[2-(naphth-2-yl)ethyl]-4-(3-trifluoromethylphenyl)-1,2,3,6-tetrahydropyridine hydrochloride and 1 l of absolute ethanol is refluxed until the product has completely dissolved. The resulting solution is cooled to 10° C. at a rate of 80° C. per hour with a stirrer speed of 500 rpm. The resulting precipitate is filtered off and dried overnight at 45° C. under vacuum.

Form II of 1-[2-(naphth-2-yl)ethyl]-4-(3-trifluoromethylphenyl)-1,2,3,6-tetrahydropyridine hydrochloride was obtained under these conditions.

In differential scanning calorimetry, the form II obtained in this preparation showed:

a solid-solid transition temperature of 153–155° C.

an enthalpy of transition of 24.1 J/g.

EXAMPLE 39

A mixture of 2 g of 1-[2-(naphth-2-yl)ethyl]-4-(3-trifluoromethylphenyl)-1,2,3,6-tetrahydropyridine hydrochloride and 50 ml of dimethyl sulfoxide is refluxed until everything has dissolved, the mixture is allowed to cool overnight and the crystalline product is then recovered and dried under vacuum at 45° C. overnight.

Form III of 1-[2-(naphth-2-yl)ethyl]-4-(3-trifluoromethylphenyl)-1,2,3,6-tetrahydropyridine hydrochloride was obtained under these conditions.

In differential scanning calorimetry, the form III obtained in this preparation showed:

a solid-solid transition temperature of 141–142° C.

an enthalpy of transition of 17.6 J/g.

EXAMPLE 40

A mixture of 100 g of 1-[2-(naphth-2-yl)ethyl]-4-(3-trifluoromethylphenyl)-1,2,3,6-tetrahydropyridine hydrochloride and 1 l of a 90/10 ethanol/water mixture is refluxed, with stirring, until the product has completely dissolved. The resulting solution is cooled from the reflux temperature to 5° C. at a rate of 10° C./hour with impeller stirring at 400 rpm. The resulting crystalline product is filtered off and dried at 45° C. under vacuum overnight.

Under these conditions, the 1-[2-(naphth-2-yl)ethyl]-4-(3-trifluoromethylphenyl)-1,2,3,6-tetrahydropyridine hydrochloride was obtained as a form I/ form III mixture in a ratio of 65.7/34.3.

In differential scanning calorimetry, the form I/III obtained in this preparation gives a thermogram which shows only the two characteristic peaks corresponding to forms I and III.

EXAMPLE 41

A solution of 3 g of 1-[2-(naphth-2-yl)ethyl]-4-(3-trifluoromethylphenyl)-1,2,3,6-tetrahydropyridine hydrochloride in 300 ml of ethanol is atomized in a Büchi mini Spray Dryer apparatus according to the parallel flow nozzle atomization principle, the pump output, the suction, the heating and the flow rate of the stream being adjusted so as to give an inlet temperature of 172° C., an outlet temperature of 107° C. and a partial vacuum of 40 mbar. Under these conditions, the product obtained shows a single broad peak in DSC with the maximum at 145° C. The particles obtained are spherical and the mean size of the very homogeneous population does not exceed 5 micrometers.

EXAMPLE 42

24 kg of 1-[2-(naphth-2-yl)ethyl]-4-(3-trifluoromethylphenyl)-1,2,3,6-tetrahydropyridine hydrochloride—form I/III, described in Example 40, are introduced into the micronization chamber (diameter 200 mm) of an ALPINE 200 AS micronizer at a rate of 25 kg/hour and at an operating pressure of 6.5 bar and the micronized product is recovered in a filter bag. The particle distribution of the resulting micronized product is such that all the particles have a size below 20 micrometers and 85% of the particles have a size below 10 micrometers.

Differential scanning calorimetry of the resulting micronized product shows that the transition temperatures are not affected by micronization. Said transitions are of the solid-solid type. The compound degrades before melting, which starts at 250° C.

EXAMPLE 43

Pharmaceutical composition containing, as the active principle, the 1-[2-(naphth-2-yl)ethyl]-4-(3-trifluoromethylphenyl)-1,2,3,6-tetrahydropyridine hydrochloride—form I/III (micronized) according to Example 42 above:

| | |
|---|---|
| Active principle | 2.192 mg |
| Corn starch | 141.208 mg |
| Anhydrous colloidal silica | 0.200 mg |
| Magnesium stearate | 0.400 mg |
| Microcrystalline cellulose | 26.000 mg |

The active principle is sieved through a 0.2 mm mesh and then premixed with the excipients. This mixture is sieved through a 0.315 mm mesh, remixed and then sieved again through a 0.315 mm mesh. After a final mixing, the composition is introduced into no. 3 gelatin capsules at a rate of 170 mg of composition containing an amount of 1-[2-(naphth-2-yl)ethyl]-4-(3-trifluoromethylphenyl)-1,2,3,6-tetrahydropyridine hydrochloride—form I/III which corresponds to 2 mg of 1-[2-(naphth-2-yl)ethyl]-4-(3-trifluoromethylphenyl)-1,2,3,6-tetrahydropyridine base.

What is claimed is:

1. A method for the treatment of diseases which cause demyelination which comprises administering to a patient in need of such treatment an effective amount of a compound of formula (I):

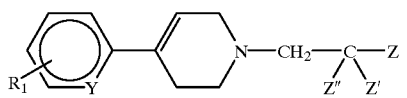

in which:

$R_1$ is a halogen or a $CF_3$, $(C_1-C_4)$alkyl or $(C_1-C_4)$alkoxy group;

Y is a nitrogen atom or a CH group;

Z' and Z" are each hydrogen or a $(C_1-C_3)$alkyl group, or one is hydrogen and the other is a hydroxyl group, or the two together are an oxo group; and Z is:
a phenyl radical;
a phenyl radical monosubstituted by a substituent X, X being:
(a) a $(C_1-C_6)$alkyl, $(C_1-C_6)$alkoxy, $(C_3-C_7)$carboxyalkyl, $(C_1-C_4)$alkoxycarbonyl$(C_1-C_6)$alkyl, $(C_3-C_7)$carboxyalkoxy or $(C_1-C_4)$alkoxycarbonyl$(C_1-C_6)$alkoxy group;
(b) a group selected from $(C_3-C_7)$cycloalkyl, $(C_3-C_7)$cycloalkoxy, $(C_3-C_7)$cycloalkylmethyl, $(C_3-C_7)$cycloalkylamino and cyclohexenyl, it being possible for said group to be substituted by a halogen, hydroxyl, $(C_1-C_4)$alkoxy, carboxyl, $(C_1-C_4)$alkoxycarbonyl, amino or mono- or di-$(C_1-C_4)$alkylamino; or
(c) a group selected from phenyl, phenoxy, phenylamino, N—$(C_1-C_3)$alkyl-phenylamino, phenylmethyl, phenylethyl, phenylcarbonyl, phenylthio, phenylsulfonyl, phenylsulfinyl and styryl, it being possible for said group to be monosubstituted or polysubstituted on the phenyl group by a halogen, $CF_3$, $(C_1-C_4)$alkyl, $(C_1-C_4)$alkoxy, cyano, amino, mono- or di-$(C_1-C_4)$alkylamino, $(C_1-C_4)$acylamino, carboxyl, $(C_1-C_4)$alkoxycarbonyl, aminocarbonyl, mono- or di-$(C_1-C_4)$alkylaminocarbonyl, amino$(C_1-C_4)$alkyl, hydroxy$(C_1-C_4)$alkyl or halogeno$(C_1-C_4)$alkyl;

a phenyl radical disubstituted by a substituent $R_2$, $R_2$ being a halogen or a hydroxyl, methyl, ethyl, $(C_3-C_6)$alkyl, $(C_1-C_4)$alkoxy or trifluoromethyl group, and by a substituent X, X being as defined above;

a 1-naphthyl or 2-naphthyl radical; or a 1-naphthyl or 2-naphthyl radical substituted in the 5-, 6-, 7- and/or 8-positions by one or two hydroxyl groups, one or two $(C_1-C_4)$alkoxy groups or a 6,7-methylenedioxy group;

or Z" is hydrogen and Z and Z' are each independently an unsubstituted or mono-, di- or tri-substituted phenyl group, or one of its pharmaceutically acceptable salts and solvates.

2. A method according to claim 1 wherein Y is CH, $R_1$ is trifluoromethyl, Z' and Z" are hydrogen and Z is as defined in claim 1.

3. A method according to claim 2 wherein Z is a 2-naphthyl, 6,7-dimethoxy-2-naphthyl or 6,7-methylenedioxy-2-naphthyl group.

4. A method according to claim 2 wherein Z is:
either a phenyl monosubstituted by a substituent X, X being as defined in claim 1;
or a phenyl disubstituted by a substituent $R_2$, $R_2$ being a halogen or a hydroxyl, methyl, ethyl, $(C_3-C_6)$alkyl, $(C_1-C_4)$alkoxy or trifluoromethyl group, and by a substituent X as defined above.

5. A method according to claim 4 wherein Z is a phenyl monosubstituted by a group X', X' being a phenyl which is unsubstituted or monosubstituted to trisubstituted by halogen, $CF_3$, $(C_1-C_4)$alkyl, $(C_1-C_4)$alkoxy, cyano, amino, mono- or di-$(C_1-C_4)$alkylamino, $(C_1-C_4)$acylamino, carboxyl, $(C_1-C_4)$alkoxycarbonyl, aminocarbonyl, mono- or di-$(C_1-C_4)$alkylaminocarbonyl, amino$(C_1-C_4)$alkyl, hydroxy$(C_1-C_4)$alkyl or halogeno$(C_1-C_4)$alkyl; or a phenyl disubstituted by a substituent $R_2$, $R_2$ being as defined in claim 4, and by a substituent X', X' being as defined above.

6. A method according to claim 4 wherein Z is a phenyl group substituted in the 3- and 4-positions by a $(C_1-C_6)$alkyl group.

7. A method according to claim 1 wherein Y is CH, $R_1$ is trifluoromethyl, Z" is hydrogen and Z and Z', which are identical, are each a phenyl group; a phenyl group substituted in the 2-, 3- or 4-position by a fluorine or chlorine atom or by a methyl, ethyl, n-propyl, i-propyl, n-butyl, i-butyl, s-butyl, t-butyl, trifluoromethyl, cyano, methoxy, methylthio, methylsulfonyl, ethoxy, ethylthio, ethylsulfonyl, $(C_1-C_3)$alkoxycarbonyl or di$(C_1-C_3)$alkylaminocarbonyl group; a phenyl group disubstituted in the 2,4-, 3,4-, 3,5- or 2,6-positions by a chlorine or fluorine atom or by a methyl, ethyl, trifluoromethyl, cyano or methoxy group; or a phenyl group trisubstituted in the 3,4,5-, 2,4,5- or 2,4,6-positions by a chlorine or fluorine atom or by a methyl, ethyl, trifluoromethyl, cyano or methoxy group.

8. A method according to claim 1 wherein the compound of formula (I) is 1-[2-(naphth-2-yl)ethyl]-4-(3-trifluoromethylphenyl)-1,2,3,6-tetrahydropyridine hydrochloride.

9. A method according to claim 8 wherein the 1-[2-(naphth-2-yl)ethyl]-4-(3-trifluoromethylphenyl)-1,2,3,6-tetrahydro-pyridine hydrochloride is in atomized or micronized form.

10. A method according to claim 8 wherein the 1-[2-(naphth-2-yl)ethyl]-4-(3-trifluoromethylphenyl)-1,2,3,6-tetra-hydropyridine hydrochloride is a micronized mixture of crystalline forms I and III in a ratio of about 66/34.

11. A method according to claim 1 wherein the compound of formula (I) is selected from the compounds:
1-(2-naphth-2-ylethyl)-4-(3-trifluoromethylphenyl)-1,2,3,6-tetrahydropyridine;
1-[2-(6,7-dimethoxynaphth-2-yl)ethyl]-4-(3-trifluoromethylphenyl)-1,2,3,6-tetrahydropyridine;
1-[2-(6,7-methylenedioxynaphth-2-yl)ethyl]-4-(3-trifluoromethylphenyl)-1,2,3,6-tetrahydropyridine;
1-[2-(4-isobutylphenyl)propyl]-4-(3-trifluoromethylphenyl)-1,2,3,6-tetrahydropyridine;
1-[(2S)-2-(4-isobutylphenyl)propyl]-4-(3-trifluoromethylphenyl)-1,2,3,6-tetrahydropyridine;
1-[(2R)-2-(4-isobutylphenyl)propyl]-4-(3-trifluoromethylphenyl)-1,2,3,6-tetrahydropyridine;
1-[2-(4-isobutylphenyl)ethyl]-4-(3-trifluoromethylphenyl)-1,2,3,6-tetrahydropyridine;

1-[2-(4-tert-butylphenyl)ethyl]-4-(3-trifluoromethylphenyl)-1,2,3,6-tetrahydropyridine;
1-[2-(4-isobutylphenyl)-2-methylpropyl]-4-(3-trifluoromethylphenyl)-1,2,3,6-tetrahydropyridine;
1-[2-(4-isopropylphenyl)ethyl]-4-(3-trifluoromethylphenyl)-1,2,3,6-tetrahydropyridine;
1-[2-(3'-chlorobiphenyl-4-yl)ethyl]-4-(3-trifluoromethylphenyl)-1,2,3,6-tetrahydropyridine;
1-[2-(2'-chlorobiphenyl-4-yl)ethyl]-4-(3-trifluoromethylphenyl)-1,2,3,6-tetrahydropyridine;
1-[2-(4'-chlorobiphenyl-4-yl)ethyl]-4-(3-trifluoromethylphenyl)-1,2,3,6-tetrahydropyridine;
1-[2-(4'-fluorobiphenyl-4-yl)ethyl]-4-(3-trifluoromethylphenyl)-1,2,3,6-tetrahydropyridine;
1-[2-(3'-trifluoromethylbiphenyl-4-yl)ethyl]-4-(3-trifluoromethylphenyl)-1,2,3,6-tetrahydropyridine;
1-[2-(4-cyclohexylphenyl)ethyl]-4-(3-trifluoromethylphenyl)-1,2,3,6-tetrahydropyridine;
1-[2-(biphenyl-4-yl)ethyl]-4-(4-fluorophenyl)-1,2,3,6-tetrahydropyridine;
1-[2-(biphenyl-4-yl)-2-methylpropyl]-4-(3-trifluoromethylphenyl)-1,2,3,6-tetrahydropyridine;
1-[2-(4-phenoxyphenyl)ethyl]-4-(3-trifluoromethylphenyl)-1,2,3,6-tetrahydropyridine;
1-[2-(4-benzylphenyl)ethyl]-4-(3-trifluoromethylphenyl)-1,2,3,6-tetrahydropyridine;
1-[2-(4-n-butylphenyl)ethyl]-4-(3-trifluoromethylphenyl)-1,2,3,6-tetrahydropyridine;
1-[2-(biphenyl-4-yl)ethyl]-4-(3-trifluoromethylphenyl)-1,2,3,6-tetrahydropyridine;
1-[2-(4-n-butoxyphenyl)ethyl]-4-(3-trifluoromethylphenyl)-1,2,3,6-tetrahydropyridine;
1-[2-(3,4-diethylphenyl)ethyl]-4-(3-trifluoromethylphenyl)-1,2,3,6-tetrahydropyridine;
1-[2-(3-methyl-4-pentylphenyl)ethyl]-4-(3-trifluoromethylphenyl)-1,2,3,6-tetrahydropyridine;
1-[2-(4-methyl-3-pentylphenyl)ethyl]-4-(3-trifluoromethylphenyl)-1,2,3,6-tetrahydropyridine;
1-[2-(3,4-diethylphenyl)ethyl]-4-(6-chloropyrid-2-yl)-1,2,3,6-tetrahydropyridine;
1-(2,2-diphenylethyl)-4-(3-trifluoromethylphenyl)-1,2,3,6-tetrahydropyridine;
1-[2,2-(4,4'-dichlorodiphenyl)ethyl]-4-(3-trifluoromethylphenyl)-1,2,3,6-tetrahydropyridine;
1-[2,2-(3,3'-bistrifluoromethyldiphenyl)ethyl]-4-(3-trifluoromethylphenyl)-1,2,3,6-tetrahydropyridine;
1-[2,2-(4,4'-dimethoxydiphenyl)ethyl]-4-(3-trifluoromethylphenyl)-1,2,3,6-tetrahydropyridine;
1-[2-(4-fluorophenyl)-2-phenylethyl]-4-(3-trifluoromethylphenyl)-1,2,3,6-tetrahydropyridine;
1-(3,3-diphenylpropyl)-4-(3-trifluoromethylphenyl)-1,2,3,6-tetrahydropyridine;
1-[2,2-(4,4'-dichlorodiphenyl)ethyl]-4-(6-chloropyrid-2-yl)-1,2,3,6-tetrahydropyridine;
1-[2-(3'-chlorobiphenyl-4-yl)-2-oxoethyl]-4-(3-trifluoromethylphenyl)-1,2,3,6-tetrahydropyridine;
1-[2-(2'-chlorobiphenyl-4-yl)-2-oxoethyl]-4-(3-trifluoromethylphenyl)-1,2,3,6-tetrahydropyridine;
1-[2-(4'-chlorobiphenyl-4-yl)-2-oxoethyl]-4-(3-trifluoromethylphenyl)-1,2,3,6-tetrahydropyridine;
1-[2-(4-isobutylphenyl)-2-oxoethyl]-4-(3-trifluoromethylphenyl)-1,2,3,6-tetrahydropyridine;
1-[2-(4-benzylphenyl)-2-oxoethyl]-4-(3-trifluoromethylphenyl)-1,2,3,6-tetrahydropyridine;
1-[2-(4-cyclohexylphenyl)-2-oxoethyl]-4-(3-trifluoromethylphenyl)-1,2,3,6-tetrahydropyridine;
1-[2-(4'-fluorobiphenyl-4-yl)-2-oxoethyl]-4-(3-trifluoromethylphenyl)-1,2,3,6-tetrahydropyridine;
1-[2-(4-n-butylphenyl)-2-oxoethyl]-4-(3-trifluoromethylphenyl)-1,2,3,6-tetrahydropyridine;
1-[2-(biphenyl-4-yl)-2-oxoethyl]-4-(3-trifluoromethylphenyl)-1,2,3,6-tetrahydropyridine;
1-[2-(4-t-butylphenyl)-2-oxoethyl]-4-(3-trifluoromethylphenyl)-1,2,3,6-tetrahydropyridine;
1-[2-(4'-trifluoromethylbiphenyl-4-yl)-2-oxoethyl]-4-(3-trifluoromethylphenyl)-1,2,3,6-tetrahydropyridine;
1-[2-(2,3'-dichlorobiphenyl-4-yl)ethyl]-4-(3-trifluoromethylphenyl)-1,2,3,6-tetrahydropyridine;
1-[2-(3-chlorobiphenyl-4-yl)ethyl]-4-(3-trifluoromethylphenyl)-1,2,3,6-tetrahydropyridine;
1-[2-(3',5'-dichlorobiphenyl-4-yl)ethyl]-4-(3-trifluoromethylphenyl)-1,2,3,6-tetrahydropyridine;
1-[2-(2',4'-dichlorobiphenyl-4-yl)ethyl]-4-(3-trifluoromethylphenyl)-1,2,3,6-tetrahydropyridine;
1-[2-(2-chlorobiphenyl-4-yl)ethyl]-4-(3-trifluoromethylphenyl)-1,2,3,6-tetrahydropyridine;
1-[2-(3'-chlorobiphenyl-4-yl)-2-methylpropyl]-4-(3-trifluoromethylphenyl)-1,2,3,6-tetrahydropyridine;
1-[2-(2-fluorobiphenyl-4-yl)propyl]-4-(3-trifluoromethylphenyl)-1,2,3,6-tetrahydropyridine;
1-[2-(4-methoxybiphenyl-3-yl)ethyl]-4-(3-trifluoromethylphenyl)-1,2,3,6-tetrahydropyridine;
1-[2-(4'-methoxybiphenyl-4-yl)ethyl]-4-(3-trifluoromethylphenyl)-1,2,3,6-tetrahydropyridine;
1-[2-(4'-hydroxybiphenyl-4-yl)ethyl]-4-(3-trifluoromethylphenyl)-1,2,3,6-tetrahydropyridine;
1-[2-(4'-ethoxycarbonylbutoxybiphenyl-4-yl)ethyl]-4-(3-trifluoromethylphenyl)-1,2,3,6-tetrahydropyridine;
1-[2-(biphenyl-3-yl)ethyl]-4-(3-trifluoromethylphenyl)-1,2,3,6-tetrahydropyridine;
1-[2-(3'-chloro-4'-fluorobiphenyl-4-yl)ethyl]-4-(3-trifluoromethylphenyl)-1,2,3,6-tetrahydropyridine;
1-[2-(2'-trifluoromethylbiphenyl-4-yl)ethyl]-4-(3-trifluoromethylphenyl)-1,2,3,6-tetrahydropyridine;
1-[2-(3,4-diisobutylphenyl)ethyl]-4-(3-trifluoromethylphenyl)-1,2,3,6-tetrahydropyridine;
1-[2-(3,4-dipropylphenyl)ethyl]-4-(3-trifluoromethylphenyl)-1,2,3,6-tetrahydropyridine;
1-[2-(4-cyclohexylphenyl)ethyl]-4-(6-chloropyrid-2-yl)-1,2,3,6-tetrahydropyridine;
1-[2-(4-isobutylphenyl)propyl]-4-(6-chloropyrid-2-yl)-1,2,3,6-tetrahydropyridine;
1-[2-(2'-trifluoromethylbiphenyl-4-yl)-2-oxoethyl]-4-(3-trifluoromethylphenyl)-1,2,3,6-tetrahydropyridine;
1-[2-(3'-trifluoromethylbiphenyl-4-yl)-2-oxoethyl]-4-(3-trifluoromethylphenyl)-1,2,3,6-tetrahydropyridine;
and their pharmaceutically acceptable salts and solvates.

12. A method according to claim 1 for the treatment of multiple sclerosis.

13. A method according to claim 2 for the treatment of multiple sclerosis.

14. A method according to claim 3 for the treatment of multiple sclerosis.

15. A method according to claim 4 for the treatment of multiple sclerosis.

16. A method according to claim 5 for the treatment of multiple sclerosis.

17. A method according to claim 6 for the treatment of multiple sclerosis.

18. A method according to claim 7 for the treatment of multiple sclerosis.

19. A method according to claim 8 for the treatment of multiple sclerosis.

20. A method according to claim 9 for the treatment of multiple sclerosis.

21. A method according to claim 10 for the treatment of multiple sclerosis.

22. A method according to claim 11 for the treatment of multiple sclerosis.

23. A method according to claim 1 wherein the compound of formula (I) is 1-[2-(naphth-2-yl)ethyl]-4-(3-trifluoromethylphenyl)-1,2,3,6-tetrahydropyridine, or a pharmaceutically acceptable salt or solvent thereof.

24. A method according to claim 23 for the treatment of multiple sclerosis.

25. A method according to claim 1 wherein Z is 1-naphthyl or 2-naphthyl or 1-naphthyl or 2-naphthyl substituted in the 5-,6-,7- and/or 8-portions by one or two hydroxyl groups, one or two ($C_1$–$C_4$)alkoxy groups or a 6,7-methylenedioxy group.

26. A method according to claim 25 wherein Y is CH and $R_1$ is $CF_3$.

27. A method according to claim 1 wherein one of Z' and Z" is hydrogen and the other is hydroxy or Z' and Z" together represent an oxo group.

28. A method according to claim 27 wherein Y is CH and $R_1$ is $CF_3$.

29. A method according to claim 1 wherein the compound of formula (I) is selected from the group consisting of:

- 1-(2-naphth-2-ylethyl)-4-(3-trifluoromethylphenyl)-1,2,3,6-tetrahydropyridine;
- 1-[2-(6,7-dimethoxynaphth-2-yl)ethyl]4-(3-trifluoromethylphenyl)-1,2,3,6-tetrahydropyridine;
- 1-[2-(6,7-methylenedioxynaphth-2-yl)ethyl]-4-(3-trifluoromethylphenyl)-1,2,3,6-tetrahydropyridine;
- 1-[2-(3'-chlorobiphenyl-4-yl)-2-oxoethyl]-4-(3-trifluoromethylphenyl)-1,2,3,6-tetrahydropyridine;
- 1-[2-(2'-chlorobiphenyl-4-yl)-2-oxoethyl]-4-(3-trifluoromethylphenyl)-1,2,3,6-tetrahydropyridine;
- 1-[2-(4'-chlorobiphenyl-4-yl)-2-oxoethyl]4-(3-trifluoromethylphenyl)-1,2,3,6-tetrahydropyridine;
- 1-[2-(4-isobutylphenyl)-2-oxoethyl]-4-(3-trifluoromethylphenyl)-1,2,3,6-tetrahydropyridine;
- 1-[2-(4-benzylphenyl)-2-oxoethyl]-4-(3-trifluoromethylphenyl)-1,2,3,6-tetrahydropyridine;
- 1-[2-(4-cyclohexylphenyl)-2-oxoethyl]-4-(3-trifluoromethylphenyl)-1,2,3,6-tetrahydropyridine;
- 1-[2-(4'-fluorobiphenyl-4-yl)-2-oxoethyl]-4-(3-trifluoromethylphenyl)-1,2,3,6-tetrahydropyridine;
- 1-[2-(4-n-butylphenyl)-2-oxoethyl]-4-(3-trifluoromethylphenyl)-1,2,3,6-tetrahydropyridine;
- 1-[2-(biphenyl-4-yl)-2-oxoethyl]-4-(3-trifluoromethylphenyl)-1,2,3,6-tetrahydropyridine;
- 1-[2-(4-t-butylphenyl)-2-oxoethyl]-4-(3-trifluoromethylphenyl)-1,2,3,6-tetrahydropyridine;
- 1-[2-(4'-trifluoromethylbiphenyl-4-yl)-2-oxoethyl]-4-(3-trifluoromethylphenyl)-1,2,3,6-tetrahydropyridine;
- 1-[2-(2'-trifluoromethylbiphenyl-4-yl)-2-oxoethyl]-4-(3-trifluoromethylphenyl)-1,2,3,6-tetrahydropyridine; and
- 1-[2-(3'-trifluoromethylbiphenyl-4-yl)-2-oxoethyl]-4-(3-trifluoromethylphenyl)-1,2,3,6-tetrahydropyridine;

or a pharmaceutically acceptable salt or solvate thereof.

* * * * *